United States Patent [19]

Franz

[11] 4,435,204

[45] Mar. 6, 1984

[54] N-ORGANO-PHOSPHONOMETHYLGLYCINE-N-OXIDES AND THE USE THEREOF TO INCREASE THE SUCROSE CONTENT OF SUGARCANE

[75] Inventor: John E. Franz, Crestwood, Mo.

[73] Assignee: Monsanto Company, St. Louis, Mo.

[21] Appl. No.: 133,379

[22] Filed: Mar. 24, 1980

Related U.S. Application Data

[60] Continuation-in-part of Ser. No. 613,707, Sep. 15, 1975, abandoned, which is a division of Ser. No. 313,706, Dec. 11, 1972, abandoned.

[51] Int. Cl.$^3$ .................................... A01N 57/00
[52] U.S. Cl. ............................................. 71/86
[58] Field of Search ............................ 71/86, 121, 76

[56] References Cited

U.S. PATENT DOCUMENTS

| | | | |
|---|---|---|---|
| 3,429,914 | 2/1969 | Crutchfield et al. | 260/501.19 |
| 3,459,759 | 8/1969 | Röchling et al. | 71/94 |
| 3,535,328 | 10/1970 | Zielinski | 71/94 |
| 3,556,762 | 1/1971 | Hamm | 71/86 |
| 3,641,042 | 2/1972 | Ayad | 71/94 |
| 3,697,251 | 10/1972 | Long et al. | 71/94 |

OTHER PUBLICATIONS

Nickell et al., "Effects of Chemicals etc.,", (1965), Haw. Sugar Technol. Conf., pp. 152–163, (1965).

*Primary Examiner*—Glennon H. Hollrah
*Attorney, Agent, or Firm*—Arnold H. Cole; Donald W. Peterson

[57] ABSTRACT

This disclosure relates to N-organo-N-phosphonomethylglycine-N-oxides and derivatives thereof. These compounds are useful to increase the sucrose content of sugarcane.

11 Claims, No Drawings

N-ORGANO-PHOSPHONOMETHYLGLYCINE-N-OXIDES AND THE USE THEREOF TO INCREASE THE SUCROSE CONTENT OF SUGARCANE

This is a continuation-in-part of application Ser. No. 613,707, filed Sept. 15, 1975, which is a division of application Ser. No. 313,706, filed Dec. 11, 1972, and both now abandoned.

This invention relates to novel N-organo-N-phosphonomethylglycine-N-oxides. These N-organo-N-phosphonomethylglycine-N-oxides are useful to increase the sucrose content of sugarcane.

The N-organo-N-phosphonomethylglycine-N-oxides of this invention are those having the formula

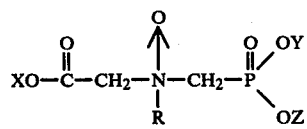

wherein X,Y and Z are each independently selected from the group consisting of hydrogen, alkyl of 1 to 8 carbon atoms, alkali metal, ammonium and alkyl ammonium in which the alkyl groups contain from 1 to 4 carbon atoms, and R is selected from the group consisting of alkyl of 1 to 12 carbon atoms, alkaryl and chlorinated alkaryl of 7 to 8 carbon atoms, phenoxyalkyl of 7 or 8 carbon atoms,

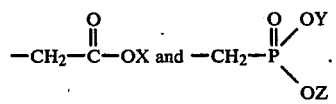

The N-oxides of the formula can be prepared by the following general procedure:

An N-organo-N-phosphonomethylgycine having the formula

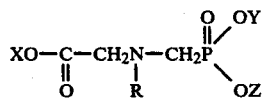

wherein X,Y,Z and R are as above defined can be oxidized to the corresponding N-oxide under acidic or basic conditions. In the acidic method the phosphonomethylglycine is suspended or dissolved in a suitable acid (i.e. acetic, trifluoroacetic, dilute sulfuric, etc.), and hydrogen peroxide or other oxidizing agent is added dropwise at a suitable temperature (0°–100° C., preferably 30°–80° C.). The reaction is exothermic, and in some media (acetic or trifluoroacetic acid), the N-oxide precipitates as a white solid. In other instances (dilute sulfuric acid), the product remains dissolved and is recovered by concentration and dilution with an appropriate solvent (e.g. ethanol).

The alkaline method is carried out by neutralizing all acidic functions of the N-organo-N-phosphonomethylglycine with strong aqueous alkali followed by addition of hydrogen peroxide or other oxidizing agent at a suitable temperature (0°–100° C., preferably 20°–60° C.). The alkali salt of the N-oxide which forms is soluble in the reaction medium and is generally recovered by concentration at reduced pressure, or it is precipitated by the addition of a suitable solvent.

It is believed that the reaction proceeds in accordance with the following equation which, for convenience, shows the oxidation of N-phosphonomethylimino diacetic acid in an acidic medium:

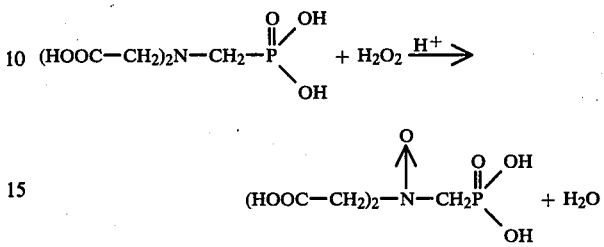

It will, of course, be apparent to those of ordinary skill in the art that the salts can then be obtained by reaction with the proper base.

The ratio of reactants employed in the process of this invention is not narrowly critical. It will be recognized by those skilled in the art that, for best yields, one must employ at least one mole of hydrogen peroxide for each mole of the N-organo-N-phosphonomethylglycine reactant. For optimum results, it is preferred to employ from two to three moles of hydrogen peroxide for each mole of the N-organo-N-phosphonomethylglycine reactant.

The temperature at which the process of this invention is conducted is not narrowly critical and can range from 0°–100° C. It has been found that if the temperature is too high, the N-oxide produced decomposes, yielding a mixture of starting material and decomposition products. It is preferred in most instances to conduct the process of this invention in the range of from 25°–80° C. in order to obtain the best yields of the N-oxide product and avoid its decomposition.

The oxidizing agents which can be employed in the process of this invention include inorganic peroxides such as hydrogen peroxide, sodium peroxide, potassium peroxide, lithium peroxide, cesium peroxide and the like; persulfuric and perboric acids and the salts of these per acids such as the sodium, lithium and potassium persulfates and perborates; peroxy organic acids and their salts such as, peroxyacetic acid, peroxybenzoic acid, m-chloroperoxybenzoic acid, 2,4-dichloroperoxybenzoic acid, peroxyformic acid, peroxytrifluoroacetic acid and the like; organic peroxides such as benzoyl peroxide, etc. and ozone.

Inasmuch as the reaction in the process of this invention is exothermic, it is preferred to employ a solvent to aid in the dissipation of the heat of reaction and to bring the reactants into more intimate contact. Solvents which can be employed in the process are those that do not react substantially with the oxidizing agent or the N-organo-N-phosphonomethylglycine reactants under the conditions employed. Such solvents are, for example, water, liquid acids such as acetic acid, trifluoroacetic acid, formic acid, propionic acid, sulfuric acid and the like; alcohols such as methanol, ethanol, isopropanol, carbitol, methyl cellosolve and the like; ethers such as dioxane, tetrahydrofuran, dimethyl ethers of ethylene glycol, diethylene glycol dimethyl ether and the like; sulfones such as sulfolane and the like, ketones such as acetone and nitriles such as acetonitrile.

The process can be conducted at atmospheric pressure, sub-atmospheric pressure or super-atmospheric pressure. For convenience and economy, it is generally preferred to conduct the process at atmospheric pressure.

The salts of N-organo-N-phosphonomethylglycine-N-oxides are prepared by partial or complete neutralization of the acid with the appropriate base, basic carbonate, ammonia or organic amine.

Detailed examples illustrating the preparation of various compounds of this invention are shown in U.S. Pat. No. 4,062,669.

In determining the regulatory effects of compounds of this invention on sugarcane, it should be noted that the appropriate rate of application can vary from about 0.112 to about 5.6 kg/hectare. Depending upon local cultural practices, sugarcane is grown for from about 9 to about 30 months before harvest, and it is thus necessary to consider both the chronological age and the maturity stage of the cane in rate determinations. Application of the treatment to the cane is generally made from about 2 to 10 weeks prior to the scheduled harvest date.

In the tests described below, individual sugarcane stalks are treated with compounds of this invention about 4–5 weeks before harvest. To avoid sampling errors, older cane, preferably 13 to 23 months old, is employed in the tests. For each compound employed, at least 5 stalks are used, processed, and the total values obtained are averaged for each stalk. In order to improve the accuracy of the analyses, only the terminal 15 joints of each stalk are used. An identical number of untreated sugarcane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in Hawaiian Planters' Record, Volume 57, pp. 133–150 (1964). The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugarcane juice.

About 38 mg. of each compound employed is dissolved in about 0.3 ml. of water which contains a small amount (about 0.1% of the final volume) of a surface active agent. The resultant solution is then applied to the whorl of each of the stalks to be tested with the exception of the untreated controls. At 4 or 5 weeks after treatment (WAT), the plants are harvested, and the top 15 joints of each stalk of a treated group and control group are removed, combined individually and analyzed as described.

In the list which follows, each of the compounds of this invention employed in a test is identified by its chemical name and is also given a letter designation. The list is followed by a tabulation of the data obtained in the tests, and said tabulation identifies the tested compound by its letter designation. Since several tests were conducted with one or more compounds of this invention, and since such tests were initiated and harvested on different dates, it will be noted that the tabulation includes separate data on the untreated control for each initiation date.

| Letter | Compound Name |
|---|---|
| A | N—phosphonomethyliminodiacetic acid-N—oxide |
| B | N—phosphonomethyliminodiacetic acid-N—oxide, monosodium salt |
| C | N,N—bis(phosphonomethyl)glycine-N—oxide |
| D | N,N—bis(phosphonomethyl)glycine-N—oxide, pentaethyl ester |
| E | N—methyl-N—phosphonomethylglycine-N—oxide |
| F | N—phosphonomethyliminodiacetic acid-N—oxide, monoisopropylamine salt |
| G | N—phosphonomethyliminodiacetic acid-N—oxide, disodium salt |
| H | N—phosphonomethyliminodiacetic acid-N—oxide, trisodium salt |
| I | N—phosphonomethyliminodiacetic acid-N—oxide, diethyl ester, hydrochloride |
| J | N,N—bis(phosphonomethyl)glycine-N—oxide, pentasodium salt |
| K | N—methyl-N—phosphonomethylglycine-N—oxide, trisodium salt |
| L | N—ethyl-N—phosphonomethylglycine-N—oxide |
| M | N—benzyl-N—phosphonomethylglycine-N—oxide |
| N | N—propyl-N—phosphonomethylglycine-N—oxide |
| O | N—isopropyl-N—phosphonomethylglycine-N—oxide |
| P | N—3,4-dichlorobenzyl-N—phosphonomethylglycine-N—oxide |
| Q | Ethyl N,N—bis(phosphonomethyl)glycinate-N—oxide, tetramethyl ester |
| R | N—isobutyl-N—phosphonomethylglycine-N—oxide, trisodium salt |
| S | N—phenethyl-N—phosphonomethylglycine-N—oxide, trisodium salt |
| T | N—dodecyl-N—phosphonomethylglycine-N—oxide, trisodium salt |
| U | N—phenoxyethyl-N—phosphonomethylglycine-N—oxide, trisodium salt |
| V | N—phosphonomethyliminodiacetic acid-N—oxide, dibutyl ester |
| W | N—phosphonomethyliminodiacetic acid-N—oxide, octyl ester |
| X | Ethyl N,N—bis(phosphonomethyl)glycine, N—oxide |
| Y | N—phosphonomethyliminodiacetic acid-N—oxide, tetrasodium salt |

The results obtained in the tests are as follows:

| | 4 WAT | | 5 WAT | |
|---|---|---|---|---|
| Compound | Juice Purity | Pol % Cane | Juice Purity | Pol % Cane |
| A | 87.67 | 13.46 | 87.69 | 13.87 |
| B | 85.57 | 12.80 | 86.64 | 13.37 |
| C | 88.63 | 14.11 | 85.96 | 12.82 |
| E | 89.32 | 14.60 | 86.93 | 13.64 |
| Control | 80.59 | 10.76 | 81.95 | 11.16 |
| A | 72.98 | 10.51 | 82.51 | 12.25 |
| E | 84.80 | 12.75 | 73.28 | 8.61 |
| Control | 61.15 | 5.64 | 64.10 | 6.87 |
| D | 81.12 | 9.94 | 76.25 | 9.17 |
| E | 94.48 | 14.80 | 85.62 | 13.67 |
| F | 81.04 | 10.87 | 83.20 | 12.68 |
| H | 87.21 | 13.38 | 83.43 | 12.09 |
| I | 82.04 | 11.70 | 87.35 | 13.75 |
| J | 81.63 | 10.41 | 75.73 | 8.75 |
| L | 83.25 | 11.59 | 82.64 | 11.66 |
| O | 78.90 | 10.26 | 84.93 | 12.34 |
| P | 83.82 | 11.99 | 84.53 | 11.24 |
| T | 86.20 | 12.14 | 87.96 | 13.64 |
| Control | 77.38 | 9.10 | 70.31 | 7.20 |
| B | 75.47 | 9.56 | 80.23 | 11.18 |
| C | 72.97 | 9.08 | 73.24 | 9.44 |
| Control | 75.51 | 9.00 | 77.56 | 9.40 |
| R | 70.28 | 8.69 | 77.63 | 10.74 |
| S | 76.83 | 10.35 | 76.94 | 10.72 |
| U | 70.28 | 8.65 | 78.48 | 10.81 |
| V | 75.77 | 9.97 | 80.70 | 10.78 |
| Control | 64.25 | 6.63 | 65.99 | 6.85 |

| Compound | 4 WAT Juice Purity | 4 WAT Pol % Cane | 5 WAT Juice Purity | 5 WAT Pol % Cane |
|---|---|---|---|---|
| M | 72.21 | 9.16 | 74.87 | 10.47 |
| N | 72.25 | 9.72 | 80.13 | 12.02 |
| Control | 61.74 | 7.91 | 62.83 | 6.13 |
| W | 78.89 | 10.81 | 83.14 | 12.68 |
| Control | 65.46 | 6.59 | 68.46 | 8.63 |
| K | 72.92 | 8.62 | 80.55 | 11.17 |
| Control | 69.79 | 7.02 | 67.85 | 7.07 |
| G | 74.83 | 7.98 | 77.37 | 9.25 |
| Q | 75.96 | 8.54 | 71.83 | 7.64 |
| Control | 72.28 | 7.50 | 70.75 | 7.51 |
| X | 75.81 | 9.75 | 79.51 | 10.80 |
| Control | 71.22 | 7.27 | 70.94 | 8.04 |
| K | 82.87 | 12.94 | 87.97 | 14.67 |
| W | 82.88 | 12.00 | 83.70 | 13.01 |
| Control | 69.73 | 7.70 | 70.57 | 6.83 |
| J | 78.71 | 9.62 | 78.55 | 10.41 |
| O | 62.67 | 6.05 | 78.59 | 11.06 |
| P | 73.04 | 8.89 | 78.26 | 10.84 |
| T | 68.43 | 6.99 | 76.32 | 9.92 |
| Control | 66.35 | 7.25 | 68.17 | 7.03 |
| R | 76.90 | 9.87 | 77.08 | 10.69 |
| Control | 69.93 | 7.35 | 54.64 | 4.86 |
| E | 80.63 | 10.52 | 82.73 | 11.96 |
| Control | 79.98 | 9.90 | 81.78 | 10.20 |
| Y | 80.04 | 11.55 | 79.63 | 11.06 |
| Control | 74.16 | 8.81 | 76.98 | 10.85 |
| Y | 87.62 | 12.61 | 86.89 | 13.29 |
| Control | 81.82 | 9.50 | 74.12 | 7.79 |
| P | 70.52 | 8.21 | 77.02 | 10.55 |
| U | 71.78 | 9.46 | 74.09 | 9.47 |
| Control | 64.99 | 6.55 | 70.76 | 7.23 |

It will be understood that useful compositions incorporating an active ingredient of this invention can be employed in either solid or liquid form. Such compositions are prepared by admixture of said active ingredient with an adjuvant such as a diluent, extender, carrier or conditioning agent to provide for application as a particulate solid, a solution or a dispersion. From the standpoint of economy and convenience, liquid compositions using water as a diluent are preferred.

The useful compositions will preferably contain from about 0.5 to about 20.0 parts by weight of a surface-active agent in order to enhance wetting, dispersion, suspension, absorption and the like. Anionic, cationic, nonionic and amphoteric types are all included within the class of surface-active agents which can be employed for such purposes.

Preferred wetting agents are alkyl benzene and alkyl naphthalene sulfonates, sulfated fatty alcohols, amines or acid amines, long chain acid esters of sodium isothionate, esters of sodium sulfosuccinate, sulfated or sulfonated fatty acid esters petroleum sulfonates, sulfonated vegetable oils, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N(long chain acid)taurates.

The inert carriers and extenders are preferably of mineral origin including natural clays, some pyrophyllites and vermiculite. Typical finely-divided solids which can be so used in compositions of this invention may be exemplified by diatomaceous earth, fuller's earth, kaolinites, attapulgite or montmorillionite clays, bentonites, synthetic silicas, calcium carbonate and calcium sulfate dihydrate. Such materials can be present in the composition in amounts of from about 3 to about 95 parts by weight.

Useful compositions of an active ingredient of this invention may also contain small amounts, up to at least 10% by weight of a variety of additives to enhance specific features. Among these additives are anti-caking or flow control agents, anti-corrosion agents, defoamers, perfumes and dyes.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A method of increasing the sucrose content of sugarcane which comprises applying to the sugarcane plants, from about 2 to about 10 weeks prior to harvest, an effective amount of a compound of the formula

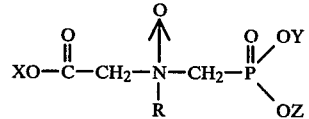

wherein X, Y and Z are each independently selected from the group consisting of hydrogen, alkyl of 1 to 8 carbon atoms, alkali metal, ammonium and alkyl ammonium in which the alkyl groups contain from 1 to 4 carbon atoms, and R is selected from the group consisting of alkyl of 1 to 12 carbon atoms, phenylalkyl and chlorinated phenylalkyl of 7 to 8 carbon atoms, phenoxyalkyl of 7 or 8 carbon atoms,

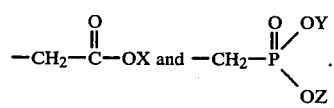

2. A method as defined in claim 1 wherein said amount is from about 0.112 to about 5.6 kg/hectare.

3. A method as defined in claim 2 wherein R is

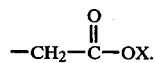

4. A method as defined in claim 2 wherein R is

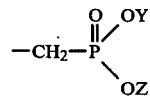

5. A method as defined in claim 2 wherein R is alkyl of 1 to 12 carbon atoms.

6. A method as defined in claim 3 wherein X,Y and Z are hydrogen.

7. A method as defined in claim 4 wherein X,Y and Z are hydrogen.

8. A method as defined in claim 5 wherein X,Y and Z are hydrogen.

9. A method as defined in claim 3 wherein X,Y and Z are selected from hydrogen and alkali metal.

10. A method as defined in claim 4 wherein X,Y and Z are selected from hydrogen and alkali metal.

11. A method as defined in claim 5 wherein X,Y and Z are selected from hydrogen and alkali metal.

* * * * *